United States Patent [19]

Cantatore et al.

[11] Patent Number: 5,039,722

[45] Date of Patent: Aug. 13, 1991

[54] PIPERIDINE-TRIAZINE COMPOUNDS FOR USE AS STABILIZERS FOR ORGANIC MATERIALS

[75] Inventors: Giuseppe Cantatore, Bitonto; Valerio Borzatta, Bologna, both of Italy

[73] Assignee: Ciba-Geigy Corporation, Ardsley, N.Y.

[21] Appl. No.: 454,083

[22] Filed: Dec. 21, 1989

[30] Foreign Application Priority Data

Dec. 23, 1988 [IT] Italy ............................... 23071 A/88

[51] Int. Cl.$^5$ ................ C08K 5/3435; C07D 401/14; C07D 413/14
[52] U.S. Cl. .............................. 524/97; 524/98; 524/100; 540/598; 544/121; 544/198; 544/209
[58] Field of Search ................. 544/121, 198, 209; 524/97, 98, 100; 540/598

[56] References Cited

U.S. PATENT DOCUMENTS

| | | | |
|---|---|---|---|
| 4,108,829 | 8/1978 | Cassandrini et al. | 540/218 |
| 4,234,728 | 11/1980 | Rody et al. | 544/198 |
| 4,426,472 | 1/1984 | Berner | 524/99 |
| 4,443,145 | 2/1984 | Wiezer et al. | 544/198 |
| 4,504,610 | 3/1985 | Fontanelli et al. | 524/100 |
| 4,530,950 | 7/1985 | Raspanti et al. | 524/100 |
| 4,816,507 | 3/1989 | Cantatore et al. | 524/100 |
| 4,863,981 | 9/1989 | Gugumus | 524/100 |
| 4,883,870 | 11/1989 | Cantatore et al. | 524/100 |

FOREIGN PATENT DOCUMENTS

| | | |
|---|---|---|
| 0117229 | 8/1984 | European Pat. Off. . |
| 0292437 | 11/1988 | European Pat. Off. . |
| 0299925 | 1/1989 | European Pat. Off. . |
| WO8101706 | 6/1981 | PCT Int'l Appl. . |

*Primary Examiner*—Kriellion S. Morgan
*Attorney, Agent, or Firm*—Luther A. R. Hall

[57] ABSTRACT

The new compounds of formula (I)

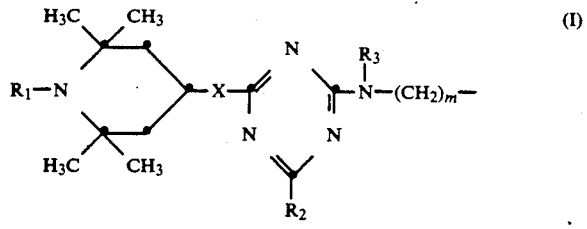

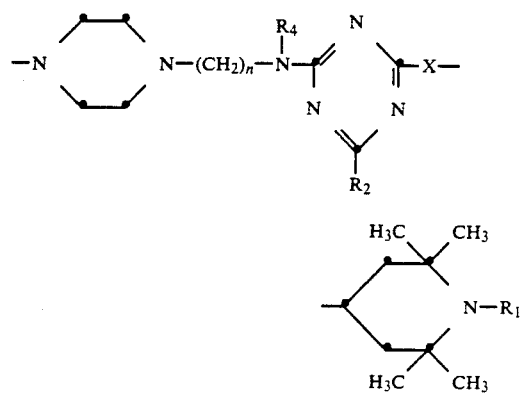

in which $R_1$ is e.g. hydrogen or methyl, $R_2$ is e.g. a group $-OR_5$ or

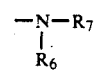

in which $R_5$ is e.g. 2,2,6,6-tetramethyl-4-piperidyl or 1,2,2,6,6-pentamethyl-4-piperidyl, $R_6$ and $R_7$ which are identical or different are e.g. $C_1$–$C_8$alkyl, tetrahydrofurfuryl, 2,2,6,6-tetramethyl-4-piperidyl or 1,2,2,6,6-pentamethyl-4-piperidyl, or $R_6$ is also hydrogen, or the group

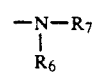

is e.g. 4-morpholinyl, $R_3$ and $R_4$ which are identical or different are e.g. hydrogen, methyl, 2,2,6,6-tetramethyl-4-piperidyl or 1,2,2,6,6-pentamethyl-4-piperidyl, m and n are e.g. 3, and X is e.g. —O— or

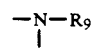

where $R_9$ is $C_1$–$C_8$alkyl, tetrahydrofurfuryl, 2,2,6,6-tetramethyl-4-piperidyl or 1,2,2,6,6-pentamethyl-4-piperidyl, are effective as light stabilizer, heat stabilizers and oxidation stabilizers for organic materials, in particular synthetic polymers.

13 Claims, No Drawings

PIPERIDINE-TRIAZINE COMPOUNDS FOR USE AS STABILIZERS FOR ORGANIC MATERIALS

The present invention relates to novel piperidine-triazine compounds, to their use as light stabilizers, heat stabilizers and oxidation stabilizers for organic materials, in particular synthetic polymers, and to organic materials thus stabilized.

It is known that synthetic polymers are subject to photooxidative degradation when they are exposed to sunlight or other sources of ultraviolet light in the presence of oxygen.

For their use in practice, it is therefore necessary to add to them suitable light stabilizers, such as benzophenone or benzotriazole derivatives, nickel complexes, substituted benzoic acid esters, alkylidenemalonates, cyanoacrylates, aromatic oxamides or sterically hindered amines.

Triazine derivatives of 2,2,6,6-tetramethyl-4-piperidylamine and their use as stabilizers for synthetic polymers have been described in U.S. Pat. Nos. 4,108,829 and 4,433,145 and in Italian Patent 1,193,659. Moreover, the preparation of N,N-bis-[3-(2,2,6,6-tetramethyl-4-piperidylamino)-propyl]-piperazine and its use as light stabilizer for polymers have been described in Belgian Patent 886,428.

In particular, the present invention relates to novel compounds of the general formula (I)

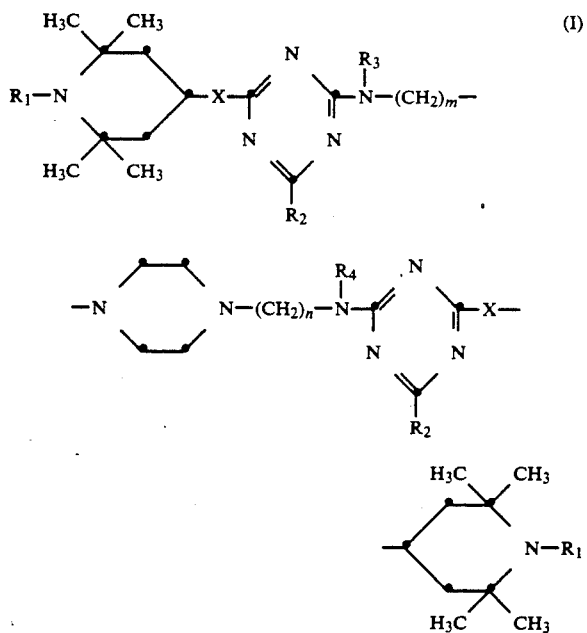

in which $R_1$ is hydrogen, $C_1$–$C_8$alkyl, O, OH, NO $CH_2CN$, $C_1$–$C_{18}$alkoxy, $C_5$–$C_{12}$cycloalkoxy, $C_3$–$C_6$alkenyl, $C_7$–$C_9$phenylalkyl which is unsubstituted or mono-, di- or tri-substituted on the phenyl by $C_1$–$C_4$alkyl, $C_1$–$C_8$acyl or $C_2$–$C_4$alkyl substituted by OH in the 2-, 3- or 4- $R_2$ is a group —$OR_5$, —$SR_5$ or

in which $R_5$ is $C_1$–$C_{18}$alkyl, $C_3$–$C_{18}$alkyl interrupted by 1, 2 or 3 oxygen atoms, $C_2$–$C_4$alkyl substituted in the 2-, 3- or 4- position by di-($C_1$–$C_4$alkyl)-amino, $C_5$–$C_{12}$cycloalkyl which is unsubstituted or mono-, di- or tri-substituted by $C_1$–$C_4$alkyl, $C_3$–$C_{18}$alkenyl, [phenyl which is unsubstituted or mono-, di- or tri-substituted by $C_1$–$C_4$alkyl, $C_7$–$C_9$phenylalkyl which is unsubstituted or mono-, di- or tri-substituted on the phenyl by $C_1$–$C_4$alkyl or a group of the formula (II)

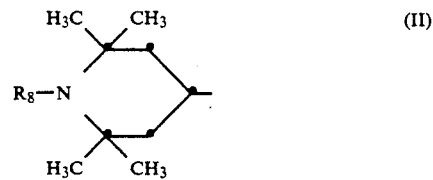

where $R_8$ has any of the definitions of $R_1$, $R_6$ and $R_7$ which can be identical or different are hydrogen, $C_1$–$C_{18}$alkyl, $C_5$–$C_{12}$cycloalkyl which is unsubstituted or mono-, di- or tri-substituted by $C_1$–$C_4$alkyl, $C_7$–$C_9$phenylalkyl which is unsubstituted or mono-, di- or tri-substituted on the phenyl by $C_1$–$C_4$alkyl, $C_2$–$C_4$alkyl which is substituted in the 2-, 3- or 4-position by OH, by $C_1$–$C_8$alkoxy or by di-($C_1$–$C_4$alkyl)-amino, $C_3$–$C_{18}$alkenyl, tetrahydrofurfuryl or a group of the formula (II), or the group

is a 5- to 7-membered heterocyclic group, $R_3$ and $R_4$ which can be identical or different are hydrogen, $C_1$–$C_{18}$alkyl, $C_5$–$C_{12}$cycloalkyl which is unsubstituted or mono-, di- or tri-substituted by $C_1$–$C_4$alkyl, $C_7$–$C_9$phenylalkyl which is unsubstituted or mono-, di- or tri-substituted on the phenyl by $C_1$–$C_4$alkyl or a group of the formula (II), m and n which can be identical or different are integers from 2 to 6 and X is —O— or

where $R_9$ is hydrogen, $C_1$–$C_{18}$alkyl, $C_5$–$C_{12}$cycloalkyl which is unsubstituted or mono-, di- or tri-substituted by $C_1$–$C_4$alkyl, $C_7$–$C_9$phenylalkyl which is unsubstituted or mono-, di- or tri-substituted on the phenyl by $C_1$–$C_4$alkyl, tetrahydrofurfuryl or a group of the formula (II).

Representative examples of $C_1$–$C_8$alkyl $R_1$ and $R_8$ are methyl, ethyl, propyl, butyl, isobutyl, pentyl, hexyl, heptyl and octyl. $C_1$–$C_4$alkyl, in particular methyl, is preferred.

Examples of $C_1$–$C_{18}$alkyl are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

Examples of $C_2$–$C_4$alkyl substituted by OH are 2-hydroxyethyl, 2-hydroxypropyl, 3-hydroxypropyl, 2-hydroxybutyl and 4-hydroxybutyl. 2-Hydroxyethyl is preferred.

Examples of $C_2$–$C_4$alkyl substituted by $C_1C_8$alkoxy, preferably $C_1$–$C_4$alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$-$C_4$alkyl substituted by di-($C_1$-$C_4$alkyl)-amino, preferably dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

Representative examples of $C_3$-$C_{18}$alkyl $R_5$ interrupted by 1, 2 or 3 oxygen atoms are 2-methoxyethyl, 2-ethoxyethyl, 2-butoxyethyl, 2-octoxyethyl, 3,6-dioxaheptyl, 3,6-dioxaoctyl, 3,6-dioxadecyl, 3,6-dioxaoctadecyl, 3,6,9-trioxadecyl and 3,6,9-trioxatridecyl, $C_3$-$C_{10}$alkyl interrupted by 1 or 2 oxygen atoms is preferred.

Representative examples of $C_1$-$C_{18}$alkoxy $R_1$ and $R_8$ are methoxy, ethoxy, propoxy, isopropoxy butoxy, isobutoxy, pentoxy, isopentoxy, hexoxy, heptoxy, octoxy, decyloxy, dodecyloxy, tetradecyloxy, hexadecyloxy and octadecyloxy. $C_6$-$C_{12}$alkoxy, in particular heptoxy or octoxy, is preferred.

Representative examples of $C_5$-$C_{12}$cycloalkoxy $R_1$ and $R_8$ are cyclopentoxy, cyclohexoxy, cycloheptoxy, cyclooctoxy, cyclodecyloxy and cyclododecyloxy. Cyclopentoxy and cyclohexoxy are preferred.

Examples of unsubstituted or substituted $C_5$-$C_{12}$cycloalkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl- Cyclohexyl is preferred.

Examples of alkenyl having up to 18 carbon atoms are allyl, 2-methylallyl, hexenyl, undecenyl and oleyl- Allyl is preferred.

In alkenyl, $R_1$, $R_5$, $R_6$, $R_7$ and $R_8$, the carbon atom in the 1-position is preferably a saturated carbon atom.

Examples of substituted phenyl are methylphenyl, dimethylphenyl, trimethylphenyl, t-butylphenyl and di-t-butylphenyl.

Examples of phenylalkyl which is unsubstituted or substituted on the phenyl are benzyl, methylbenzyl, dimethylbenzyl, t-butylbenzyl and 2-phenylethyl.

Acyl $R_1$ and $R_8$ having up to 8 carbon atoms can be an aliphatic or aromatic group- Representative examples are formyl, acetyl, propionyl, butyryl, pentanoyl, hexanoyl, octanoyl, benzoyl, acryloyl and crotonyl, $C_1$-$C_8$alkanoyl, $C_3$-$C_8$alkenoyl and benzoyl are preferred- Acetyl is particularly preferred.

A 5-membered to 7-membered heterocyclic group

can also contain a further heteroatom, for example nitrogen or oxygen; representative examples are 1-pyrrolidyl, 1-piperidyl, 4-morpholinyl, 4-methyl-1-piperazinyl, 1-hexahydroazepinyl, 5,5,7-trimethyl-1-homopiperazinyl and 4,5,5,7-tetramethyl-1-homopiperazinyl- 4-Morpholinyl is preferred.

$R_1$ is preferably hydrogen, $C_1$-$C_4$alkyl, OH, $C_6$-$C_{12}$alkoxy, $C_5$-$C_8$cycloalkoxy, allyl, benzyl, acetyl or 2-hydroxyethyl, in particular hydrogen or methyl.

Those compounds of the formula (I) are preferred in which $R_2$ is a group —$OR_5$, —$SR_5$ or

in which $R_5$ is $C_1$-$C_{12}$alkyl, $C_3$-$C_{10}$alkyl interrupted by 1, 2 or 3 oxygen atoms, $C_2$-$C_3$alkyl substituted in the 2- or 3-position by di-($C_1$-$C_4$alkyl)-amino, $C_5$-$C_8$cycloalkyl which is unsubstituted or mono-, di- or tri-substituted by $C_1$-$C_4$alkyl, $C_3$-$C_{12}$alkenyl, phenyl, benzyl or a group of the formula (II), $R_6$ and $R_7$ which can be identical or different are hydrogen, $C_1$-$C_{12}$alkyl, $C_5$-$C_8$cycloalkyl which is unsubstituted or mono-, di- or tri-substituted by $C_1$-$C_4$alkyl, benzyl, $C_2$-$C_3$alkyl substituted in the 2- or 3-position by OH, by $C_1$-$C_4$alkoxy or by di-($C_1$-$C_4$alkyl)-amino, allyl, oleyl, tetrahydrofurfuryl or a group of the formula (II), or the group

is 1-pyrrolidyl, 1-piperidyl, 4-morpholinyl, 4-methyl-1-piperazinyl or 1- hexahydroazepinyl, $R_3$ and $R_4$ which can be identical or different are hydrogen, $C_1$-$C_{12}$alkyl, $C_5$-$C_8$cycloalkyl which is unsubstituted or mono-, di- or tri-substituted by $C_1$-$C_4$alkyl, benzyl or a group of the formula (II), m and n which can be identical or different are 2 or 3, and X is —O— or

where $R_9$ is hydrogen, $C_1$-$C_{12}$alkyl, $C_5$-$C_8$cycloalkyl which is unsubstituted or mono- , di- or tri-substituted by $C_1$-$C_4$alkyl, benzyl, tetrahydrofurfuryl or a group of the formula (II).

Those compounds of the formula (I) are particularly preferred in which $R_2$ is a group —$OR_5$ or

in which $R_5$ is $C_1$-$C_8$alkyl, $C_4$-$C_{10}$alkyl interrupted by 1 or 2 oxygen atoms, $C_2$-$C_3$alkyl substituted in the 2- or 3-position by dimethylamino or diethylamino, cyclohexyl which is unsubstituted or mono-, di- or tri-substituted by $C_1$-$C_4$alkyl, allyl, undecenyl, phenyl, benzyl, or a group of the formula (II), $R_6$ and $R_7$ which can be identical or different are hydrogen, $C_1$-$C_{12}$alkyl, cyclohexyl which is unsubstituted or mono-, di- or tri-substituted by $C_1$-$C_4$alkyl, benzyl, $C_2$-$C_3$alkyl substituted in the 2- or 3- position by OH, by methoxy, by ethoxy, by dimethylamino or by diethylamino, allyl, tetrahydrofurfuryl or a group of the formula (II) or the group

is 4- morpholinyl or 4- methyl-1piperazinyl, $R_3$ and $R_4$ which can be identical or different are hydrogen, $C_1$-$C_8$alkyl, cyclohexyl which is unsubstituted or mono-, di- or tri-substituted by $C_1$-$C_4$alkyl, benzyl or a group of the formula (II), m and n which can be identical or different are 2 or 3, and X is —O— or

where $R_9$ is hydrogen, $C_1-C_{12}$alkyl, cyclohexyl which is unsubstituted or mono-, di- or tri-substituted by $C_1-C_4$alkyl, benzyl, tetrahydrofurfuryl or a group of the formula (II).

Those compounds of the formula (I) are of special interest in which $R_2$ is a group $-OR_5$ or

in which $R_5$ is $C_1-C_4$alkyl, 2,2,6,6-tetramethyl-4-piperidyl or 1,2,2,6,6-pentamethyl-4-piperidyl, $R_6$ and $R_7$ which can be identical or different are $C_1-C_8$alkyl, cyclohexyl, benzyl, $C_2-C_3$alkyl substituted in the 2- or 3-position by methoxy, by ethoxy, by dimethylamino or by diethylamino, allyl, tetrahydrofurfuryl, 2,2,6,6-tetramethyl-4-piperidyl or 1,2,2,6,6-pentamethyl-4-piperidyl, or $R_6$ is also hydrogen or the group

is 4-morpholinyl, $R_3$ and $R_4$ which can be identical or different are hydrogen, $C_1-C_4$alkyl, cyclohexyl, 2,2,6,6-tetramethyl-4-piperidyl or 1,2,2,6,6-pentamethyl-4-piperidyl, m and n are 3, and X is —O— or

where $R_9$ is $C_1-C_8$alkyl, cyclohexyl, benzyl, tetrahydrofurfuryl, 2,2,6,6-tetramethyl-4-piperidyl or 1,2,2,6,6-pentamethyl-4-piperidyl.

Those compounds of the formula (I) are of particular interest in which $R_1$ is hydrogen or methyl, $R_2$ is a group $-OR_5$ or

in which $R_5$ is 2,2,6,6-tetramethyl-4-piperidyl or 1,2,2,6,6-pentamethyl-4-piperidyl, $R_6$ and $R_7$ which can be identical or different are $C_1-C_8$ alkyl, tetrahydrofurfuryl, 2,2,6,6-tetramethyl-4-piperidyl or 1,2,2,6,6-pentamethyl-4-piperidyl, or $R_6$ is also hydrogen, or the group

is 4morpholinyl, $R_3$ and $R_4$ which can be identical or different are hydrogen, methyl, 2,2,6,6-tetramethyl-4-piperidyl or 1,2,2,6,6-pentamethyl-4-piperidyl, m and n are 3, and X is —O— or

where $R_9$ is $C_1-C_8$alkyl, tetrahydrofurfuryl, 2,2,6,6-tetramethyl-4-piperidyl or 1,2,2,6,6-pentamethyl-4-piperidyl.

The compounds of the formula (I) can be prepared by processes known per se, for example as described in U.S. Pat. No. 4,108,829, by reacting, in any order, cyanuric chloride with the compounds of the formulae (IIIa)–(IIIc)

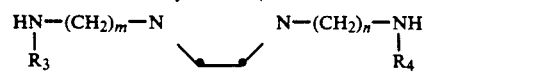

using the appropriate molar ratios.

If $R_1$ and $R_8$ are methyl, the compounds of the formula (I) are preferably prepared by reacting the corresponding compounds where $R_1$ and $R_8$=H with formaldehyde and formic acid or with formaldehyde and hydrogen in the presence of a hydrogenation catalyst such as e.g. palladium or platinum.

In these reactions, melamine >NH groups which may be present can also be methylated under certain conditions.

The reactions of cyanuric chloride with the compounds of the formulae (IIIa)–(IIIc) are preferably carried out in an aromatic hydrocarbon solvent such as e.g. toluene, xylene or trimethylbenzene at a temperature from $-20°$ to $40°$ C., preferably from $-10°$ to $20°$ C., for the substitution of the first Cl, from $40°$ to $100°$ C., preferably from $50°$ to $90°$ C., for the substitution of the second Cl and from $100°$ C. to $200°$ C., preferably from $120°$ to $180°$ C., for the substitution of the third Cl.

The hydrohalic acid released in the various reactions is neutralized preferably by an inorganic base for example sodium or potassium hydroxide or carbonate in quantities at least equivalent to the acid released.

The intermediates (IIIa)–(IIIc) used are commercial products or products which can be prepared by known processes.

As mentioned at the outset, compounds of the formula (I) are highly effective in improving the light stability, heat stability and oxidation stability of organic materials, in particular synthetic polymers or copolymers. Examples of such organic materials which can be stabilized are:

1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high-density polyethylene (HDPE), low-density polyethylene (LDPE) and linear low-density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, such as, for example, ethylene/propylene, linear low-density polyethylene (LLDPE) and its mixtures with low-density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidenenorbornene; as well as mixtures of such copolymers and their mixtures with polymers mentioned in 1) above, for example polypropylene/ethylene-propylene copolymers, LDPE/EVA, LDPE/EAA, LLDPE/EVA and LLDPE/EAA.

3a. Hydrocarbon resins (for example $C_5$–$C_9$) and hydrogenated modifications thereof (for example tackyfiers).

4. Polystyrene, poly-(p-methylstyrene)- poly-(α-methylstyrene).

5. Copolymers of styrene or o-methylstyrene with dienes or acrylic derivatives, such as, for example, styrene/acrylonitrile, styrene/alkyl methacrylate, styrene/maleic anhydride, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene or o-methylstyrene such as, for example, styrene on polybutadiene, styrene on polybutadiene-styrene or polybutadiene acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS, MBS, ASA or AES polymers.

7. Halogen-containing polymers, such as polychloroprene, chlorinated rubbers, chlorinated or sulfochlorinated polyethylene, copolymers of ethylene and chlorinated ethylene, epichlorohydrin homo- and copolymers, polymers from halogen-containing vinyl compounds, as for example polyvinyl chloride, polyvinylidene chloride, polyvinyl fluoride, polyvinylidene fluoride, as well as copolymers thereof, as for example vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene or polyamides.

14. Polyurethanes which are derived from polyethers, polyesters or polybutadienes with terminal hydroxyl groups on the one hand and on the other hand aliphatic or aromatic polyisocyanates, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6/10, 6/9, polyamide 6/6, 6/12 and 4/6, polyamide 11, polyamide 12, aromatic polyamides obtained by condensation of m-xylenediamine and adipic acid; polyamides prepared from hexamethylenediamine and isophthalic and/or terephthalic acid and optionally an elastomer as modifier, for example poly-2,4,4-trimethyl-hexamethylene-terephthalamide or poly-m-phenylene-isophthalamide. Further, copolymers of the aforementioned polyamides with polyolefins, olefin copolymers, ionomers or chemically bonded or grafted elastomers; or with polyethers, such as for instance, with polyethylene glycols, polypropylene glycols or polytetramethylene glycols. Polyamides or copolyamides modified with EPDM or ABS-Polyamides condensed during processing (RIM-polyamide systems).

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly-[2,2- (4- hydroxyphenyl)propane] terephthalate and polyhydroxybenzoates as well as block copolyether-esters derived from polyethers having hydroxyl end groups.

18. Polycarbonates and polyester-carbonates.

19. Polysulfones, polyether-sulfones and polyether ketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer-homologous manner, such as cellulose acetates, cellulose propionates and cellulose butyrates, or cellulose ethers, such as methylcellulose; rosins and their derivatives.

27. Mixtures of polymers as mentioned above, for example PP/EPDM, polyamide 6/EPDM or ABS, PVC/EVA, PVC/ABS, PVC/MBS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6-6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubbers, for example natural latex or latexes of carboxylated styrene/butadiene copolymers.

The compounds of the formula (I) are particularly suitable for improving the light stability, heat stability and oxidation stability of polyolefins, especially polyethylene and polypropylene. The compounds of the formula (I) can be used in mixtures with organic materials in various proportions depending on the nature of the material to be stabilized, on the end use and on the presence of other additives.

In general, it is appropriate to use, for example, 0.01 to 5 % by weight of the compounds of the formula (I), relative to the weight of the material to be stabilized, preferably from 0.05 to 1 %.

The compounds of the formula (I) can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

In general, the compounds of formula (I) can be added to the polymeric materials before, during or after polymerization or cross-linking of said materials.

The materials stabilized with the products of the formula (I) can be used for the production of moldings, films, tapes, monofilaments, surface coatings and the like.

If desired, other conventional additives for synthetic polymers, such as antioxidants, UV absorbers, nickel stabilizers, pigments, fillers, plasticizers, antistatic agents, flameproofing agents, lubricants, corrosion inhibitors and metal deactivators, can be added to the mixtures of the compounds of the formula (I) with the organic materials.

Particular examples of additives which can be used in a mixture with the compounds of the formula (I) are:

1 Antioxidants 1.1. Alkylated monophenols- for example 2-6 di-tert-butyl-4- methylphenol, 2- tert-butyl-4,6- dimethylphenol- 2,6- di-tert-butyl-4- ethylphenol, 2,6- di-tert-butyl-4- n-butylphenol, 2,6- di-tert-butyl-4- isobutylphenol, 2,6- dicyclopentyl-4- methylphenol, 2- (α-methylcyclohexyl)-4,6-dimethylphenol, 2,6- dioctadecyl-4- methylphenol, 2,4,6- tricyclohexylphenol, 2,6- di-tert-butyl-4- methoxymethylphenol, 2,6- dinonyl-4- methylphenol.

1.2. Alkylated hydroquinones- for example 2,6- di-tert-butyl-4- methoxyphenol, 2,5- di-tert-butylhydroquinone, 2,5- di tert-amylhydroquinone, 2,6- diphenyl-4- octadecyloxyphenol.

1.3. Hydroxylated thiodiohenyl ethers- for example 2,2'-thiobis(6- tert-butyl-4- methylphenol), 2,2'-thiobis(4- octylphenol), 4,4'-thiobis(6- tert-butyl-3-methylphenol), 4,4' thiobis(6- tert-butyl-2- methylphenol).

1.4. Alkylidenebisphenols- for example 2,2'-methylenebis(6- tert-butyl-4-methylphenol), 2,2'-methylenebis(6- tert-butyl-4- ethylphenol), 2,2'-methylenebis[4- methyl-6- (α-methylcyclohexyl)-phenol]- 2,2'-methylene-bis(4-methyl-6-cyclohexylphenol), 2,2'-methylenebis(6- nonyl-4- methylphenol), 2,2' methylenebis(4,6- di-tert-butylphenol), 2,2'-ethylidenebis-(4,6-di-tert-butylphenol)-2,2'-ethylidenebis(6-tert-butyl-4-isobutylphenol), 2,2' methylenebis[-6- (α-methylbenzyl)-4- nonylphenol], 2,2'-methylenebis[6-(α,α-dimethylbenzyl)-4- nonylphenol], 4,4'-methylene-bis-(2,6-di-tert-butylphenol), 4,4'-methylenebis(6- tert-butyl-2- methyl-phenol), 1,1- bis(5- tert-butyl-4- hydroxy-2- methylphenyl)butane, 2,6-bis (3- tert-butyl 5-methyl-2- hydroxybenzyl)-4- methylphenol, 1,1,3- tris(5-tert-butyl-4- hydroxy-2- methylphenyl)butane, 1,1- bis(5- tert-butyl-4-hydroxy-2- methylphenyl)-3-n-dodecylmercaptobutane, ethylene glycol bis[3,3-bis(3'-tert-butyl-4'-hydroxyphenyl)butyrate], bis(3- tert-butyl-4-hydroxy-5- methylphenyl)-dicyclopentadiene, bis[2- (3'-tert-butyl-2'-hydroxy-5'-methylbenzyl)-6- tert-butyl-4- methylphenyl]terephthalate.

1.5. Benzyl compounds, for example 1,3,5- tris(3,5- di tert-butyl-4-hydroxybenzyl)-2,4,6- trimethylbenzene-bis(3-5- di-tert-butyl-4- hydroxy-benzyl) sulfide- isooctyl 3-5- di tert-butyl-4- hydroxy-benzylmercapto-acetate, bis(4- tert-butyl 3- hydroxy-2,6- dimethylbenzyl) dithiolterephthalate, 1,3,5- tris(3,5- di-tert-butyl-4- hydroxyphenzyl) isocyanurate, 1,3,5- tris(4- tert-butyl-3-hydroxy-2,6- dimethylbenzyl) isocyanurate, di-octadecyl 3,5-di-tert-butyl-4- hydroxy-benzylphosphonate, calcium salt of monoethyl 3,5- di-tert-butyl-4- hydroxybenzylphosphonate, 1,3,5- tris(3,5-dicyclohexyl-4- hydroxyphenzyl) isocyanurate.

1.6. Acylaminophenols, for example lauric acid 4-hydroxyanilide, stearic acid 4- hydroxyanilide, 2,4- bis-(octylmercapto)-6- (3,5- di tert-butyl-4-hydroxyanilino)-s-triazine, octyl N-(3,5- di-tert-butyl-4- hydroxyphenyl) carbamate.

1.7. Esters of β-(3-5- di-tert-butyl-4- hydroxyphenyl)-propionic acid with mono- or polyhydric alcohols, e-g- with methanol- diethylene glycol, octadecanol, triethylene glycol- 1,6- hexanediol, pentaerythritol, neopentyl glycol, tris(hydroxyethyl) isocyanurate, thiodiethylene glycol, N,N'-bis(hydroxyethyl)oxalic acid diamide.

1.8. Esters of β-(5 tert-butyl-4- hydroxy-3 methylphenol)propionic acid with mono- or polyhydric alcohols, e-g- with methanol, diethylene glycol, octadecanol, triethylene glycol, 1,6- hexanediol, pentaerythritol, neopentyl glycol- tris(hydroxyethyl) isocyanurate, thiodiethylene glycol, N,N'bis(hydroxyethyl)oxalic acid diamide.

1.9. Esters of β-(3-5- dicyclohexyl-4- hydroxyphenyl)propionic acid with mono- or polyhydric alcohols, e.g. with methanol, diethylene glycol, octadecanol, triethylene glycol, 1-6- hexanediol, pentaerythritol, neopentyl glycol-tris(hydroxyethyl) isocyanurate, thiodiethylene glycol, N,N'-bis(hydroxyethyl)oxalic acid diamide.

1.10. amides of β-(3,5-di-tert-butyl-4-hydroxyphenyl)propionic acid e.g. N,N' bis(3,5- di-tert-butyl-4-hydroxyphenylpropionyl)hexamethylenediamine, N,N'-bis(3,5- di-tert-butyl-4 hydroxyphenypropionyl)-trimethylenediamine, N,N'-bis(3,5- di-tert-butyl-4- hydroxyphenylpropionyl)hydrazine.

2. UV absorbers and light stabilizers 2.1. 2- (2'-Hydroxyphenyl)benzotriazoles, for example the 5'-methyl, 3',5'-di-tert-butyl, 5'-tert-butyl, 5' (1,1,3,3- tetramethylbutyl), 5-chloro-3',5'-di-tert-butyl-5- chloro-3 - tert-butyl-5'-methyl, 3'-sec-butyl-5'-tert-butyl, 4'-octoxy-3',5'-di-tert-amyl and 3',5'-bis(α,α-dimethylbenzyl) derivatives.

2.2. 2- Hydroxybenzophenones, for example the 4-hydroxy, 4- methoxy, 4 -octoxy, 4- decyloxy, 4-dodecyloxy, 4- benzyloxy, 4,2',4'-trihydroxy and 2'-hydroxy-4,4'-dimethoxy derivatives.

2.3. Esters of substituted -and unsubstituted benzoic acids, for example 4- tert-butylphenyl salicylate, phenyl salicylate, octylphenyl salicylate, dibenzoylresorcinol, bis(4- tert-butylbenzoyl)resorcinol, benzoylresorcinol, 2,4- di-tert-butylphenyl 3,5- di-tert-butyl-4-hydroxybenzoate and hexadecyl 3,5- di-tert-butyl-4- hydroxybenzoate.

2.4. Acrylates, for example ethyl α-cyano-β,β-diphenylacrylate, isooctyl α-cyano-β,β-diphenylacrylate, methyl α-carbomethoxycinnamate- methyl α-cyano -β-methyl p-methoxycinnamate, butyl α-cyano-β-methyl p-methoxy cinnamate, methyl α-carbomethoxy p-methoxycinnamate and N-(β-carbomethoxy-β-cyanovinyl)-β-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4- hydroxy-3,5- di-tert-butylbenzylphosphonic acid monoalkyl esters, e.g. of the methyl or ethyl ester, nickel complexes of ketoximes, e.g. of 2-hydroxy-4- methylphenyl undecyl ketoxime, nickel complexes of 1-phenyl-4-lauroyl-5-hydroxypyrazole, with or without additional ligands.

2.6. Sterically hindered amines- for example bis(2,2,6,6- tetramethyl-piperidyl) sebacate- bis(1,2,2,6,6- pentamethylpiperidyl) sebacate, bis-(1,2,2,6,6-pentamethylpiperidyl) n-butyl-3,5- di-tert-butyl-4- hydroxy-benzylmalonate, the condensation product of 1-hydroxyethyl-2,2,6,6-tetramethyl-4-hydroxypiperidine and succinic acid, the condensation product of N,N'-bis(2,2,6,6- tetramethyl-4- piperidyl)-hexamethylenediamine and 4- tert-octylamino-2-6- dichloro-1,3,5- triazine, tris(2,2,6,6- tetramethyl-4- piperidyl) nitrilotriacetate, tetrakis(2,2,6,6- tetramethyl-4-piperidyl) 1,2,3,4-butanetetracarboxylate, 1,1'-(1,2-ethanediyl)bis-(3,3,5,5-tetramethylpiperazinone).

2.7. Oxalic acid diamides, for example 4,4'-dioctyloxyoxanilide, 2,2'-dioctyloxy-5,5'-di-tert-butyloxanilide, 2-2'-didodecyloxy-5,5'-di-tert-butyloxanilide, 2-ethoxy-2-ethyloxanilide, N,N'-bis(3- dimethylaminopropyl)oxalamide, 2- ethoxy-5- tert-butyl-2'-ethyloxanilide and its mixtures with 2- ethoxy-2'-ethyl-5,4'-di-tert-butyloxanilide and mixtures of ortho- and paramethoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine.

3, Metal deactivators- for example N,N'-diphenyloxalic acid diamide, N-salicylal-N'-salicyloylhydrazine, N,N'-bis(salicyloyl)hydrazine, N,N'-bis(3,5- di-tert-butyl-4- hydroxyphenylpropionyl)hydrazine, 3-salicyloylamino-1,2,4- triazole, bis(benzylidene)oxalodihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4- di-tert-butylphenyl) phosphite, diisodecyl pentaerythritol diphosphite, bis(2,4-di-tert-butylphenyl) pentaerythritol diphosphite, tristearyl sorbitol triphosphite, tetrakis(2,4-di-tert-butylphenyl) 4,4'-biphenylenediphosphonite, 3,9- bis(2,4-di-tert-butylphenoxy)-2,4,8,10- tetraoxa-3,9- diphosphaspiro[5-5]undecane.

5. Peroxide scavengers, for example esters of β-thiodipropionic acid, for example the lauryl, stearyl, myristyl or tridecyl esters, mercaptobenzimidazole or the zinc salt of 2 mercaptobenzimidazole, zinc dibutyldithiocarbamate, dioctadecyl disulfide, pentaerythritol tetrakis(β-dodecylmercapto)propionate.

6. Polyamide stabilizers- for example copper salts in combination with iodides and/or phosphorus compounds and salts of divalent manganese.

7. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example Ca stearate, Zn stearate, Mg stearate, Na ricinoleate and K palmitate, antimony pyrocatecholate or zinc pyrocatecholate.

8. Nucleating agents, for example 4-tert-butyl-benzoic acid, adipic acid, diphenylacetic acid.

9. Fillers and reinforcing agents, for example calcium carbonate, silicates, glass fibers, asbestos- talc, kaolin, mica, barium sulfate, metal oxides and hydroxides, carbon black, graphite.

10. Other additives, for example plasticizers, lubricants, emulsifiers, pigments, optical brighteners, flameproofing agents, antistatic agents and blowing agents.

In order to illustrate the present invention more clearly, several examples of the preparation of compounds of the formula (I) are described below; these examples are given by way of illustration only and do not imply any restriction.

The compounds described in Examples 1, 2, 6 and 7 pertain to a preferred embodiment of the present invention.

EXAMPLE 1

Preparation of the compound

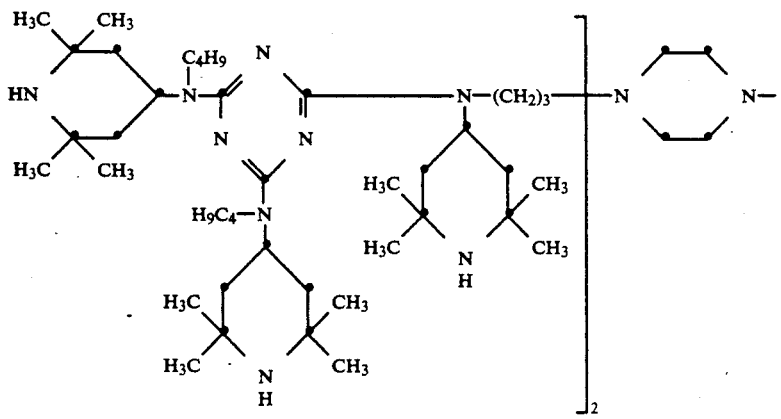

42.89 g (0.08 mol) of 2- chloro-4,6- bis[N-(2,2,6,6- tetramethyl-4- piperidyl) -butylamino]-1,3,5- triazine- 19.15 g (0.04 mol) of N,N'-bis-[3-(2,2,6,6- tetramethyl-4- piperidylamino)-propyl]-piperazine and 6.4 g (0.16 mol) of sodium hydroxide in 250 ml of mesitylene are heated under reflux for 20 hours, with azeotropic removal of the water of reaction.

The mixture is cooled to about 50° C. and filtered, and the filtrate is washed with water. The solution is then dried over sodium sulfate and evaporated in vacuo (2 mbar).

The residue is taken up in acetone, from which the product of melting point 174°-176° C. crystallizes.

Analysis for $C_{86}H_{164}N_{20}$
Calculated: C=69.87%; H=11.18%; N=18.95%;
Found: C=70.25%; H=11.23%; N=18.78%.

EXAMPLES 2-4

Following the procedure described in Example 1 and using the appropriate reagents, the following compounds of the formula

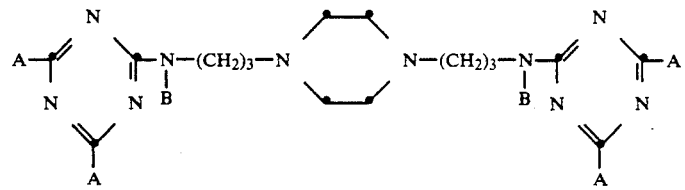

are prepared:

| Example | A | B | Melting point (°C.) |
|---|---|---|---|
| 2 | (HN-tetramethylpiperidyl with tetramethylpiperidyl-NH substituent) | 2,2,6,6-tetramethylpiperidyl-NH | 310–312 |
| 3 | $H_9C_4$—N— (2,2,6,6-tetramethylpiperidyl-NH) | —H | 98–101 |

| Example | A | B | Melting point (°C.) |
|---|---|---|---|
| 4 | (structure) | —H | 333–336 |

EXAMPLE 5

Preparation of the compound

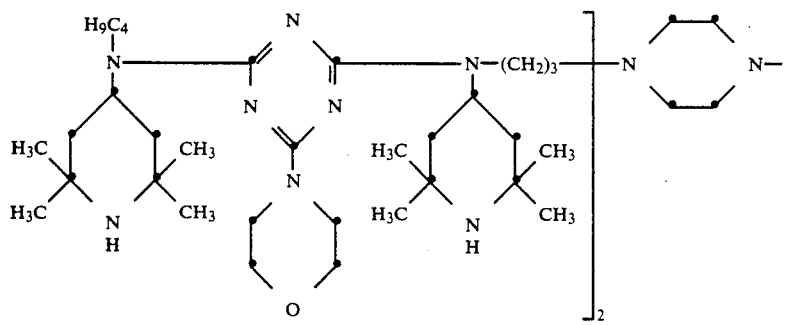

Following the procedure described in Example 1, but using 82.19 g (0.2 mol) of 2-chloro-4-morpholino-6-[N-(2,2,6,6-tetramethyl-4-piperidyl)-butylamino]-1,3,5-triazine, 47.88 g (0.1 mol) of N,N'-bis-[3-(2,2,6,6-tetramethyl-4-piperidylamino)-propyl]-piperazine and 16 g (0-4 mol) of sodium hydroxide in 500 ml of mesitylene, the product of melting point 160°–164° C. is obtained.

Analysis for $C_{68}H_{126}N_{18}O_2$
Calculated: C=66.52%; H=10.34%; N=20.53%;
Found: C=66.40%; H=10.28%; N=20.34%.

EXAMPLE 6

Preparation of the compound

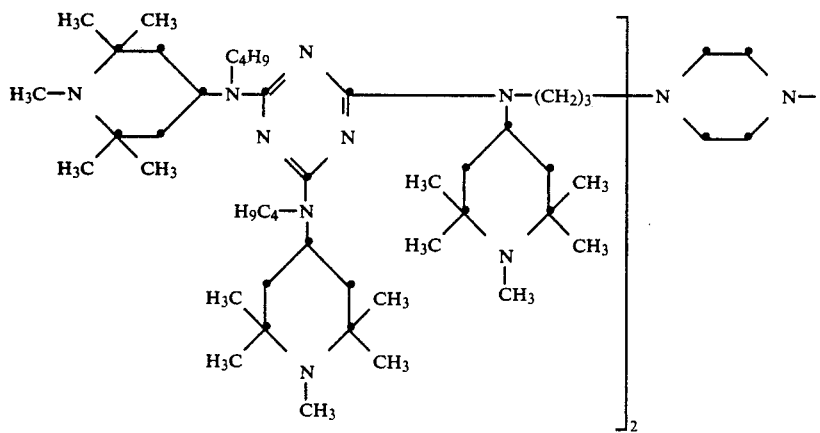

A mixture consisting of 3-17 g (0-069 mol) of formic acid and a solution obtained by dissolving 2-16 g (0-072 mol) of paraformaldehyde in 20 ml of an aqueous 2% sodium hydroxide solution is added slowly in the course of 2 hours to a solution, heated to 115° C., of 14.78 g (0.01 mol) of the product from Example 1 in 35 ml of xylene; during the addition, the water added and the water of reaction are removed azeotropically at the same time.

The mixture is cooled to 60° C., a solution of 3.31 g of sodium hydroxide in 25 ml of water is added, and the mixture is heated for 1 hour at 60° C. After the aqueous phase has been separated off, the mixture is washed with water, dried over sodium sulfate and then evaporated in vacuo, giving a product of melting point 160°–163° C.

Analysis for $C_{92}H_{176}N_{20}$
Calculated: C=70.72%; H=11.35%; N=17.93%;
Found: C=70.37%; H=11.32%; N=17.84%.

EXAMPLES 7-9

Following the procedure illustrated in Example 6, but using the appropriate reagents and molar ratios, the following compounds of the formula

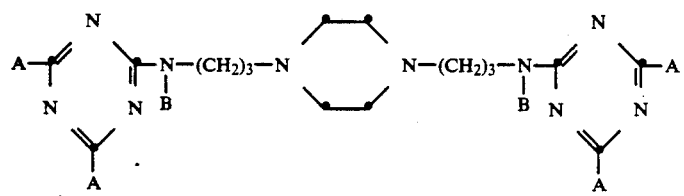

are prepared:

The specimens are checked at regular intervals by folding them by 180° in order to determine the time (in hours) required for fracturing them. The results obtained are given in Table 1.

TABLE 1

| Stabilizer | Time to fracture (hours) |
| --- | --- |
| without stabilizer | 250 |
| compound from Example 1 | 1,530 |
| compound from Example 2 | 1,100 |
| compound from Example 6 | 1,810 |
| compound from Example 7 | 1,600 |

| Example | A | B | Melting point (°C.) |
| --- | --- | --- | --- |
| 7 | (structure with H3C, CH3, H3C—N, H3C, CH3, H3C, CH3, H3C, CH3, N, CH3) | (structure with H3C, CH3, H3C, CH3, N, CH3) | 295-297 |
| 8 | (structure with H3C, CH3, H3C—N, H3C, CH3, H3C, CH3, H3C, CH3, N, CH3) | —H | 310-312 |
| 9 | (structure H9C4—N—, H3C, CH3, H3C, CH3, N, CH3) | —H | 92-94 |

EXAMPLE 10

Antioxidant action on polypropylene plaques 1 g of each of the compounds indicated in Table 1 and 1 g of calcium stearate are mixed in a slow mixer with 1000 g of polypropylene powder of melt index=2 g/10 minutes (measured at 230° C. and 2.16 kg).

The mixtures are extruded twice at 200°-220° C. to give polymer granules which are then converted into plaques of 1 mm thickness by compression-molding at 230° C. for 6 minutes.

The plaques are then punched using a DIN 53451 mold, and the specimens obtained are exposed in a forced-circulation air oven maintained at a temperature of 135° C.

EXAMPLE 11

Light-stabilizing agent in polypropylene tapes 1 g of each of the compounds indicated in Table 2, 0-5 g of tris(2,4-di-t-butylphenyl) phosphite, 0-5 g of pentaerythritol tetrakis-3- (3,5- di-t-butyl-4-hydroxyphenyl)-propionate and 1 g of calcium stearate are mixed in a slow mixer with 1000 g of polypropylene powder of melt index=2 g/10 minutes (measured at 230° C. and 2.16 kg).

The mixtures are extruded at 200°-220° C. to give polymer granules which are then converted into stretched tapes of 50 μm thickness and 2.5 mm width, using a pilot-type apparatus (®Leonard-Sumirago (VA) Italy) and operating under the following conditions:

| extruder temperature | 210-230° C. |
|---|---|
| head temperature | 240-260° C. |
| stretch ratio | 1:6 |

The tapes thus prepared are exposed, mounted on a white card, in a Weather-O-Meter 65 WR (ASTM G26-77) with a black panel temperature of 63° C.

The residual tenacity is measured on samples, taken after various times of exposure to light, by means of a constant-speed tensometer; the exposure time (in hours) needed to halve the initial tenacity ($T_{50}$) is then calculated.

Tapes prepared under the same conditions as indicated above, but without the addition of stabilizer, are exposed for comparison. The results obtained are shown in Table 2:

TABLE 2

| Stabilizer | $T_{50}$ (hours) |
|---|---|
| without stabilizer | 500 |
| compound from Example 1 | 2,490 |
| compound from Example 2 | 2,660 |
| compound from Example 3 | 2,490 |
| compound from Example 6 | 2,310 |
| compound from Example 8 | 2,330 |

What is claimed is:

1. A compound of formula (I)

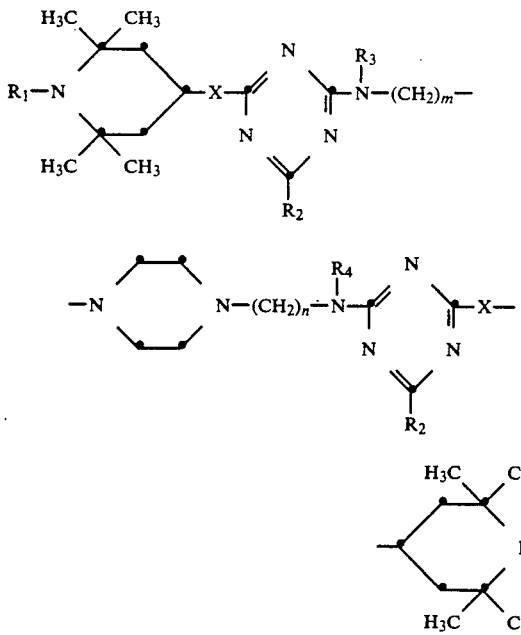

in which $R_1$ is hydrogen, $C_1$-$C_8$alkyl, O, OH, NO, $CH_2CN$, $C_1$-$C_{18}$alkoxy, $C_5$-$C_{12}$cycloalkoxy, $C_3$-$C_5$alkenyl, $C_7$-$C_9$phenylalkyl which is unsubstituted or mono-, di- or tri-substituted on the phenyl by $C_1$-$C_4$alkyl, $C_1$-$C_8$acyl or $C_2$-$C_4$alkyl substituted by OH in the 2-, 3- or 4-position, $R_2$ is a group —$OR_5$, —$SR_5$ or

in which $R_5$ is $C_1$-$C_{18}$alkyl, $C_3$-$C_{18}$alkyl interrupted by 1, 2 or 3 oxygen atoms, $C_2$-$C_4$alkyl substituted in the 2-, 3- or 4-position by di-($C_1$-$C_4$alkyl)-amino, $C_5$-$C_{12}$cycloalkyl which is unsubstituted or mono-, di- or tri-substituted by $C_1$-$C_4$alkyl, $C_3$-$C_{18}$alkenyl, phenyl which is unsubstituted or mono-, di- or tri-substituted by $C_1$-$C_4$alkyl, $C_7$-$C_9$phenylalkyl which is unsubstituted or mono-, di- or tri-substituted on the phenyl by $C_1$-$C_4$alkyl or a group of the formula (II)

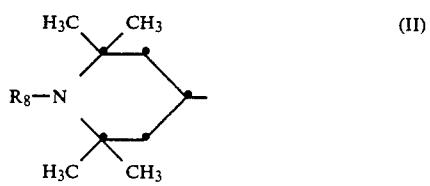

where $R_8$ has any of the definitions of $R_1$, $R_6$ and $R_7$ which are identical or different are hydrogen, $C_1$-$C_{18}$alkyl, $C_5$-$C_{12}$cycloalkyl which is unsubstituted or mono-, di- or tri-substituted by $C_1$-$C_4$alkyl, $C_7$-$C_9$phenylalkyl which is unsubstituted or mono-, di- or tri-substituted on the phenyl by $C_1$-$C_4$alkyl, $C_2$-$C_4$alkyl which is substituted in the 2-, 3- or 4-position by OH, by $C_1$-$C_8$alkoxy or by di-($C_1$-$C_4$alkyl)-amino, $C_3$-$C_{18}$alkenyl, tetrahydrofurfuryl or a group of the formula (II), or the group

is a 5- to 7-membered heterocyclic group which is 1-pyrrolidyl, 1-piperidyl, 4-morpholinyl, 4-methyl-1-piperazinyl, 1-hexahydroazepinyl, 5,5,7-trimethyl-1-homopiperazinyl or 4,5,5,7-tetramethyl-1-homopiperazinyl, $R_3$ and $R_4$ which are identical or different are hydrogen, $C_1$-$C_{18}$alkyl, $C_5$-$C_{12}$cycloalkyl which is unsubstituted or mono-, di- or tri-substituted by $C_1$-$C_4$alkyl, $C_7$-$C_9$phenylalkyl which is unsubstituted or mono-, di- or tri-substituted on the phenyl or $C_1$-$C_4$alkyl or a group of the formula (II), m and n which are identical or different are integers from 2 to 6 and X is —O— or

where $R_9$ is hydrogen, $C_1$-$C_{18}$alkyl, $C_5$-$C_{12}$cycloalkyl which is unsubstituted or mono-, di- or tri-substituted by $C_1$-$C_4$alkyl, $C_7$-$C_9$phenylalkyl which is unsubstituted or mono-, di- or tri-substituted on the phenyl by $C_1$-$C_4$alkyl, tetrahydrofurfuryl or a group of the formula (II).

2. A compound of the formula (I) according to claim 1, in which $R_1$ is hydrogen, $C_1$-$C_4$alkyl, OH, $C_5$-$C_{12}$alkoxy, $C_5$-$C_8$cycloalkoxy, allyl, benzyl, acetyl or 2-hydroxyethyl.

3. A compound of the formula (I) according to claim 1, in which R₂ is a group —OR₅, —SR₅ or

in which R₅ is C₁–C₁₂alkyl, C₃–C₁₀alkyl interrupted by 1, 2 or 3 oxygen atoms, C₂–C₃alkyl substituted in the 2- or 3-position by di-(C₁–C₄alkyl)-amino, C₅–C₈cycloalkyl which is unsubstitued or mono-, di- or tri-substituted by C₁–C₄alkyl, C₃–C₁₂alkenyl, phenyl, benzyl or a group of the formula (II), R₆ and R₇ which are identical or different are hydrogen, C₁–C₁₂alkyl, C₅–C₈cycloalkyl which is unsubstituted or mono-, di- or tri-substituted by C₁–C₄, benzyl, C₂–C₃alkyl substituted in the 2- or 3-position by OH, by C₁–C₄alkoxy or by di-(C₁–C₄alkyl)-amino, allyl, oleyl, tetrahydrofurfuryl or a group of the formula (II), or the group

is 1-pyrrolidyl, 1-piperidyl, 4-morpholinyl, 4-methyl-1-piperazinyl or 1-hexahydroazepinyl, R₃ and R₄ which are identical or different are hydrogen, C₁–C₁₂alkyl, C₅–C₈cycloalkyl which is unsubstituted or mono-, di- or tri-substituted by C₁–C₄alkyl, benzyl or a group of the formula (II), m and n which are identical or different are 2 or 3, and X is —O— or

where R₉ is hydrogen, C₁–C₁₂alkyl, C₅–C₈cycloalkyl which is unsubstituted or mono-, di- or tri-substituted by C₁–C₄alkyl, benzyl, tetrahydrofurfuryl or a group of the formula (II).

4. A compound of the formula (I) according to claim 1, in which R₂ is a group —OR₅ or

in which R₅ is C₁–C₈alkyl, C₄–C₁₀alkyl interrupted by 1 or 2 oxygen atoms, C₂–C₃alkyl substituted in the 2- or 3-position by dimethylamino or diethylamino, cyclohexyl which is unsubstituted or mono-, di- or tri-substituted by C₁–C₄alkyl, allyl, undecenyl, phenyl, benzyl, or a group of the formula (II), R₆ and R₇ which are identical or different are hydrogen, C₁–C₁₂alkyl, cyclohexyl which is unsubstituted or mono-, di- or tri-substituted by C₁–C₄alkyl, benzyl, C₂–C₃alkyl substituted in the 2- or 3-position by OH, by methoxy, by ethoxy, by dimethylamino or by diethylamino, allyl, tetrahydrofurfuryl or a group of the formula (II) or the group

is 4-morpholinyl or 4-methyl-1-piperazinyl, R₃ and R₄ which are identical or different are hydrogen, C₁–C₈alkyl, cyclohexyl which is unsubstituted or mono-, di- or tri-substituted by C₁–C₄alkyl, benzyl or a group of the formula (II), m and n which are identical or different are 2 or 3, and X is —O— or

where R₉ is hydrogen, C₁–C₁₂alkyl, cyclohexyl which is unsubstituted or mono-, di- or tri-substituted by C₁–C₄alkyl, benzyl, tetrahydrofurfuryl or a group of the formula (II).

5. A compound of the formula (I) according to claim 1, in which R₂ is a group —OR₅ or

in which R₅ is C₁–C₄alkyl, 2,2,6,6-tetramethyl-4-piperidyl or 1,2,2,6,6-pentamethyl-4-piperidyl, R₆ and R₇ which are identical or different are C₁–C₈alkyl, cyclohexyl, benzyl, C₂–C₃alkyl substituted in the 2- or 3-position by methoxy, by ethoxy, by dimethylamino or by diethylamino, allyl, tetrahydrofurfuryl, 2,2,6,6-tetramethyl-4-piperidyl or 1,2,2,6,6-pentamethyl-4-piperidyl, or R₆ is also hydrogen or the group

is 4-morpholinyl, R₃ and R₄ which are identical or different are hydrogen, C₁–C₄alkyl, cyclohexyl, 2,2,6,6-tetramethyl-4-piperidyl or 1,2,2,6,6-pentamethyl-4-piperidyl, m and n are 3, and X is —O— or

where R₉ is C₁–C₈alkyl, cyclohexyl, benzyl, tetrahydrofurfuryl, 2,2,6,6-tetramethyl-4-piperidyl or 1,2,2,6,6-pentamethyl-4-piperidyl.

6. A compound of the formula (I) according to claim 1, in which R₁ is hydrogen or methyl, R₂ is a group —OR₅ or

in which R₅ is 2,2,6,6-tetramethyl-4-piperidyl or 1,2,2,6,6-pentamethyl-4-piperidyl, R₆ and R₇ which are identical or different are C₁–C₈alkyl, tetrahydrofurfuryl, 2,2,6,6-tetramethyl-4-piperidyl or 1,2,2,6,6-pentamethyl-4-piperidyl, or R₆ is also hydrogen, or the group

is 4-morpholinyl, R₃ and R₄ which are identical or different are hydrogen, methyl, 2,2,6,6-tetramethyl-4-piperidyl or 1,2,2,6,6-pentamethyl-4-piperidyl, m and n are 3, and X is —O— or

where $R_9$ is $C_1$-$C_8$alkyl, tetrahydrofurfuryl, 2,2,6,6-tetramethyl-4-piperidyl or 1,2,2,6,6-pentamethyl-4-piperidyl.

7. The compound of the formula

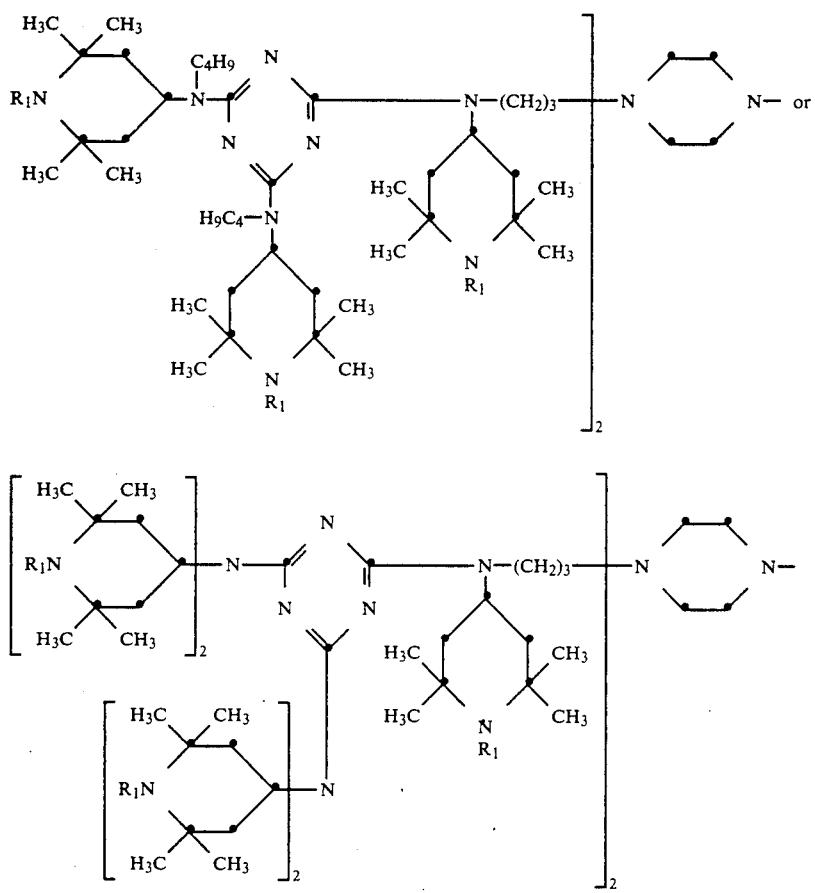

in which the radicals $R_1$ are equal and are hydrogen or methyl, according to claim 1.

8. A composition containing an a polymer, oil, fat or wax susceptible to degradation induced by light, heat or oxidation and an effective stabilizing amount of a compound of the formula (I) according to claim 1.

9. A composition according to claim 8, wherein the polymer is a synthetic polymer.

10. A composition according to claim 9 which, in addition to the compound of the formula (I), also contains other conventional additives for synthetic polymers.

11. A composition according to claim 8, wherein the polymer is a polyolefin.

12. A composition according to claim 8, wherein the polymer is polyethylene or polypropylene.

13. A method for stabilizing an a polymer, oil, fat or wax against degradation induced by light, heat or oxidation, which comprises incorporating into said organic material an effective stabilizing amount of a compound of the formula (I) according to claim 1.

* * * * *